United States Patent [19]
Jain et al.

[11] Patent Number: 6,010,712
[45] Date of Patent: Jan. 4, 2000

[54] THERAPEUTIC USE OF BFGF TO TREAT CONDITIONS INVOLVING ADHESION OF CYTOTOXIC WHITE CELLS TO ENDOTHELIUM

[75] Inventors: Rakesh K. Jain, Boston, Mass.; Robert J. Melder, Gaithersburg, Md.; Gerald C. Koenig, Somerville; Lance L. Munn, Medford, both of Mass.

[73] Assignees: The General Hospital Corporation, Boston, Mass.; Massachusetts Institute of Technology, Cambridge, Mass.

[21] Appl. No.: 08/921,115

[22] Filed: Aug. 29, 1997

Related U.S. Application Data

[60] Provisional application No. 60/025,483, Aug. 29, 1996.

[51] Int. Cl.[7] .......................................................... A61F 2/02
[52] U.S. Cl. .............................................................. 424/423
[58] Field of Search ............................................ 424/423

[56] References Cited

PUBLICATIONS

Melder et al., During Angiogenesis, Vascular endothelium Growth factor and Basic Fibroblast Growth factor regulate Natural Killer Cell Adhesion to Tumour Endothelium Abstract only, Nat. Med. (NY) 2(9), 992–997, 1996.

Kitayama et al., Suppressive Effect of Basic Fibroblast Growth Factor on Transendothelial Emigration of CD4(x) T–Lymphocyte, Abstract only, Cancer Reseach, 54(17), 4729–33, 1994.

Griffioen et al., "Endothelial Intercellular Adhesion Molecule–1 Expression Is Suppressed in Human Malignancies: The Role of Angiogenic Factors", Cancer Research 56:1111–1117, Mar. 1, 1996.

Griffioen et al., "Tumor Angiogenesis Is Accompanied by a Decreased Inflammatory Response of Tumor–Associated Endothelium", Blood 88:667–673, Jul. 15, 1996.

Jain et al., "Leukocyte–endothelial Adhesion and Angiogenesis in Tumors", Cancer and Metastasis Reviews 15:195–204, 1996.

*Primary Examiner*—Carlos A. Azpuru
*Attorney, Agent, or Firm*—Fish & Richardson P.C.

[57] ABSTRACT

A method of treating a condition involving vascular adhesion of cytotoxic white cells by (a) identifying an animal suspected of having a condition involving vascular adhesion of cytotoxic white cells and (b) administering to the animal an amount of bFGF sufficient to decrease cell surface expression of ICAM-I or VCAM-I on endothelial cells, thereby reducing adhesion of cytotoxic white cells to vascular endothelium.

22 Claims, 7 Drawing Sheets

THERAPEUTIC USE OF BFGF TO TREAT CONDITIONS INVOLVING ADHESION OF CYTOTOXIC WHITE CELLS TO ENDOTHELIUM

Under 35 USC §119(e)(1), this application claims the benefit of prior U.S. provisional application 60/025,483, filed Aug. 29, 1996.

The field of the invention is modulation of an immune response, e.g., to decrease inflammation.

BACKGROUND OF THE INVENTION

Both xenogeneic and syngeneic activated natural killer (A-NK) cells adhere to tumor vasculature when injected into the tumor's blood supply. However, the molecular and biophysical mechanisms of this localization in tumor vasculature have not been defined. Previous studies have suggested that localization of these cells in tumor vessels is due primarily to their adhesive characteristics rather than mechanical or hemodynamic considerations. Studies of NK cell adhesion in vitro have documented the involvement of both β1 and β2 integrins in the absence of shear stress or rate-limited binding conditions. Lymphocyte adhesion to activated endothelium under a range of shear stress conditions has been shown to involve multiple cellular adhesion molecules (CAMs): in particular, intracellular and vascular CAMS (ICAM-1 and VCAM-1) and E-selectin. In addition, several studies have documented increased expression of these CAMs in the tumor vasculature and significant infiltration of lymphocytes, especially in the periphery of growing tumors. These observations suggest that the tumor microenviroment may modulate the expression of CAMs on the endothelial cells of tumor vessels and may facilitate adhesion of certain lymphocytes.

SUMMARY OF THE INVENTION

In a number of pathological conditions (e.g., sepsis, inflammation, cancer, ischemia-reperfusion injury) and medically beneficial procedures (e.g., organ transplantation, tissue engineering), certain adhesion molecules are upregulated. These molecules can serve as recognition/binding sites for various white blood cells in the circulating blood (e.g., cytotoxic lymphocytes), with potentially harmful consequences.

The invention features a method of treating a condition involving vascular adhesion of cytotoxic white cells (e.g., sepsis, inflammation, ishemia-repurfusion injury, or rejection of a transplanted organ, cell or tissue) by (1) identifying an animal suspected of having a condition involving vascular adhesion of cytotoxic white cells and (2) administering to the animal, such as a human, an amount of basic fibroblast growth factor (bFGF) sufficient to decrease cell surface expression of ICAM-I or VCAM-I on endothelial cells so that adhesion of cytotoxic white cells to vascular endothelium is decreased. The bFGF can be administered to the animal by any means known in the art, such as systemically, intravenously, via an expression vector or a cell containing the vector, or via an implant which can allow slow release of the bFGF.

In another aspect, the invention features a method of reducing adhesion of cytotoxic white cells to vascular endothelium of a transplant (e.g., an organ, tissue, or cell) by treating the transplant ex vivo with an amount of bFGF sufficient to decrease cell surface expression of ICAM-I or VCAM-I on endothelial cells of the transplant, thereby reducing adhesion of cytotoxic white cells to vascular endothelium of the transplant. This will reduce the risk of rejection of the transplant by the host's immune system. The bFGF can be administered by any means known in the art, including via perfusion, via an expression vector or a cell containing the vector, or via an implant which can allow slow release of the bFGF.

By "expression vector" is meant any nucleic acid molecule or virus containing regulatory elements or reporter genes for the purpose of expression of a given gene in prokaryotic or eukaryotic cells or organisms. Such vectors can be introduced into a cell by means of molecular biological techniques. After introduction into the cell, this nucleic acid can exist extrachromosomally or become integrated into the host genome.

Unless otherwise defined, all technical and scientific terms used herein have the same meaning as commonly understood by one of ordinary skill in the art to which this invention belongs. Although methods and materials described herein can be used to practice the present invention, other similar or equivalent methods and material known to one skilled in the art can also be used. All publications, patent applications, patents, and other references mentioned herein are incorporated by reference in their entirety. In case of conflict, the present specification, including definitions, will control. The materials, methods, and examples described herein are illustrative only and not intended to be limiting.

Other features and advantages of the invention will be apparent from the following detailed description, and from the claims.

DETAILED DESCRIPTION

Figure 1A:
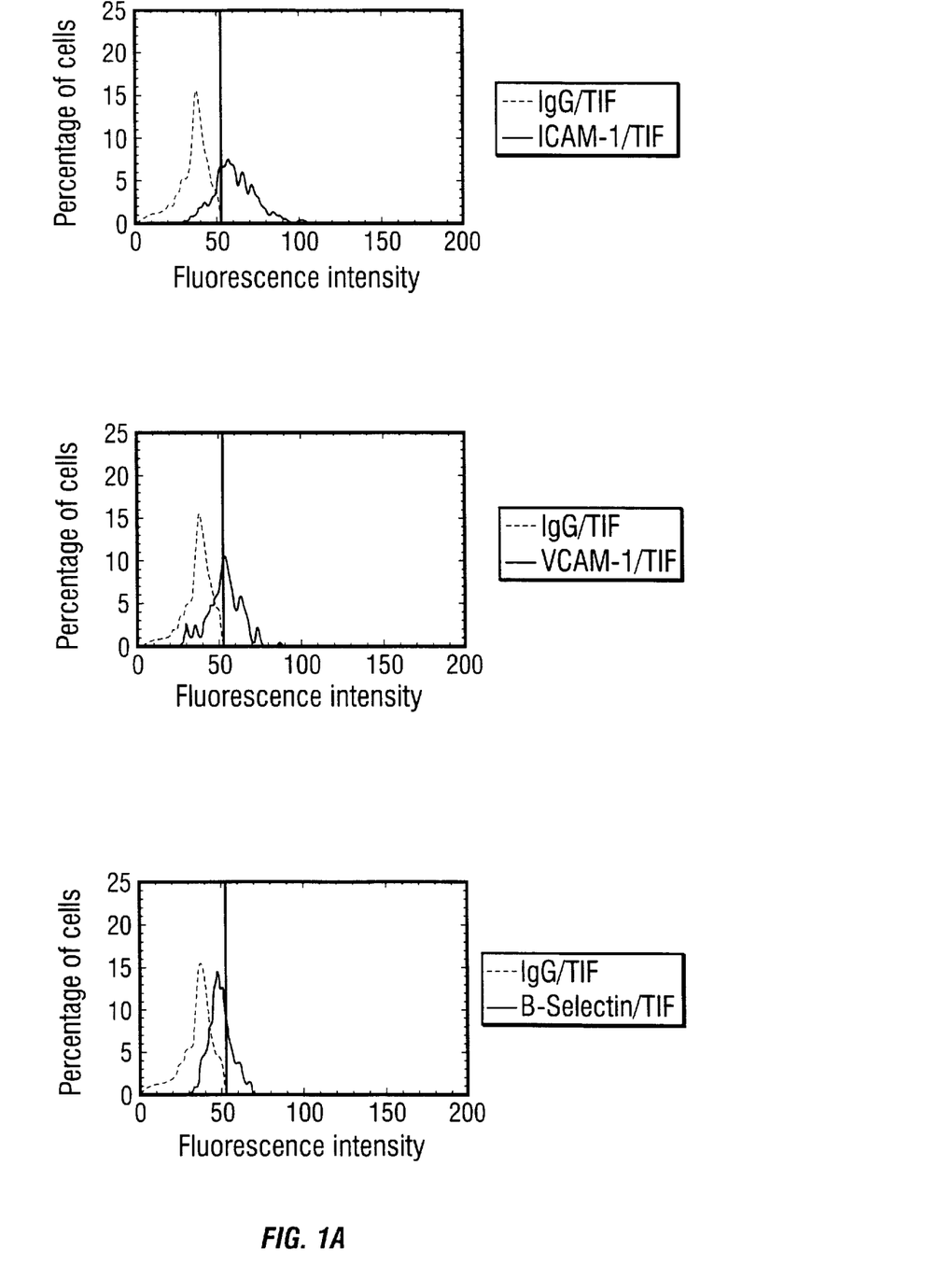
FIG. 1a is an intensity histogram of HUVEC cells stained for ICAM-1, VCAM-1, and E-selectin in response to TIF treatment.
Figure 1B:
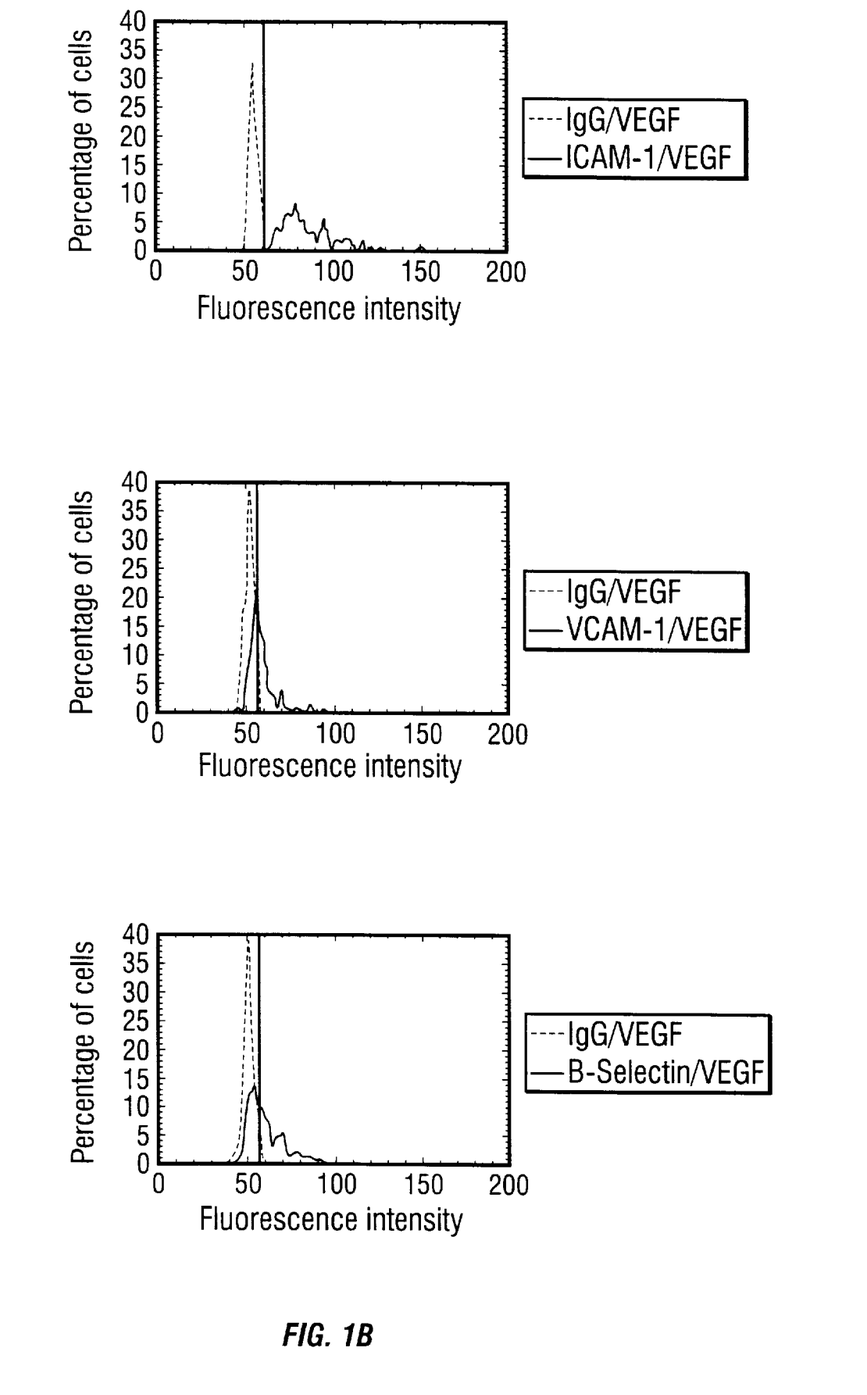
FIG. 1b is an intensity histogram of HUVEC cells stained for ICAM-1, VCAM-1, and E-selectin in response to VEGF treatment.
Figure 1C:
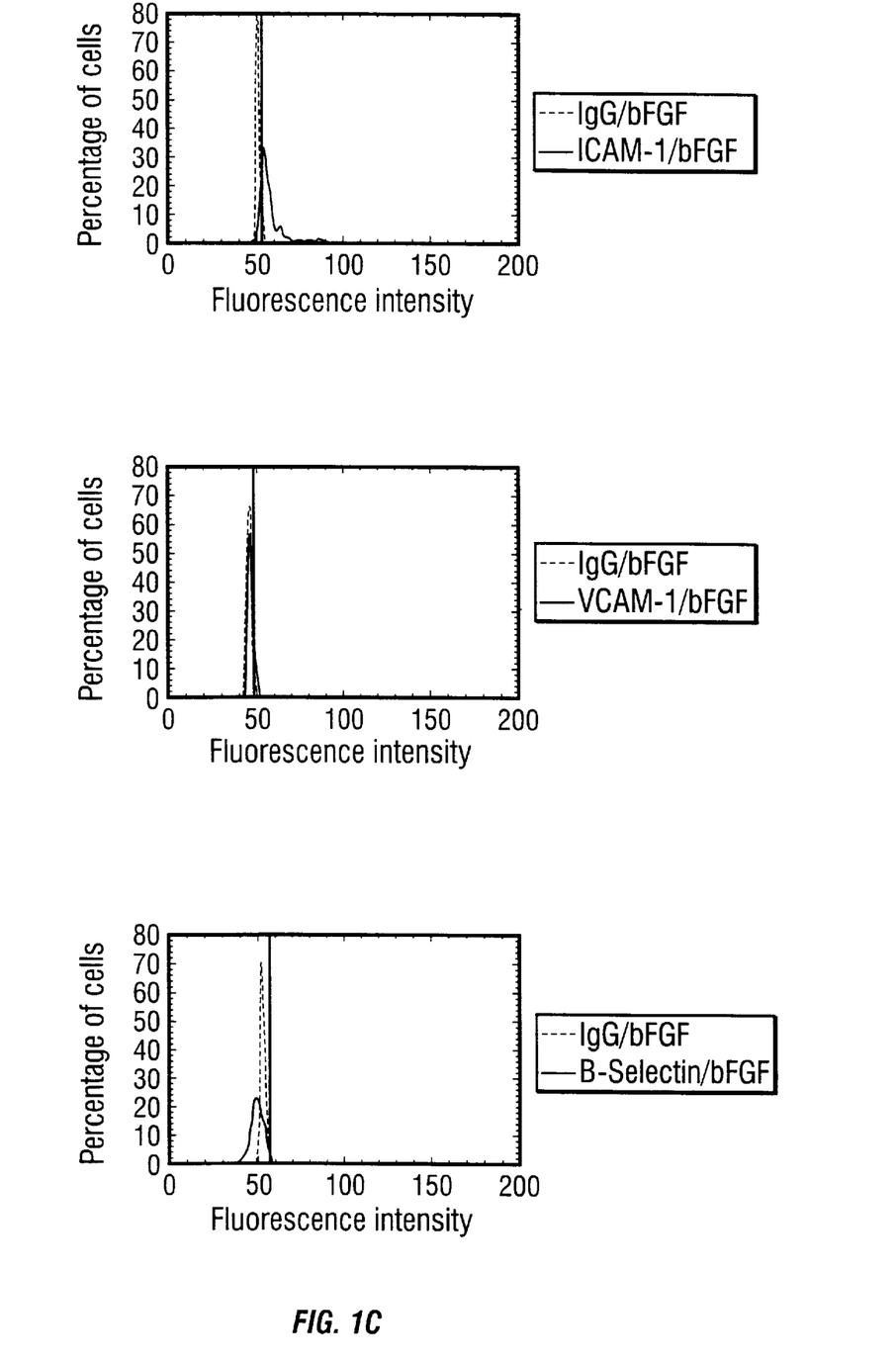
FIG. 1c is an intensity histogram of HUVEC cells stained for ICAM-1, VCAM-1, and E-selectin in response to bFGF treatment.

Tumor interstitial fluid contains a variety of agents that could potentially mediate increased expression of CAMs on endothelial cells, including both inflammatory cytokines and angiogenesis factors. We hypothesized that because A-NK cells bound to angiogenic vessels in normal transplanted tissue and tumor, and because vascular endothelial growth factor (VEGF) and basic fibroblast growth factor (bFGF) are present in healing wounds and tumors, some of these cytokines may be mediators of increased CAM expression following tumor interstitial fluid (TIF) treatment. To test this hypothesis, human umbilical vein endothelial cells (HUVEC) were treated with VEGF (35 ng/ml) or bFGF (10 ng/ml) in culture medium for 24 hours and evaluated for the expression of CAMs. Following TIF treatment, increased levels of ICAM-1, VCAM-1 and E-selectin expression were seen following VEGF exposure; however, no change was observed in P-selectin expression (FIG. 1b). Exposure of HUVEC to bFGF failed to produce an increase in any CAM expression (FIG. 1c).

We hypothesized that the molecules in the tumor microenvironment, particularly tumor angiogenesis factors, are responsible for modulation of CAM expression in tumor vessels. Two in vitro approaches we used to examine this hypothesis: quantification of CAM expression on endothelial monolayers following exposure to tumor interstitial fluid (TIF) or known angiogenesis factors, and characterization of the cellular binding kinetics and the molecular mechanisms of adhesion to treated endothelial cells under laminar flow over a range of physiological shear stress conditions. Further, cranial windows that permit the in vitro observation of lymphocyte interactions with angiogenic vasculature were used to verify the involvement of various CAMs in the localization process.

Tumor interstitial fluid modulation of CAM expression. The first goal of this study was to determine whether expression of various endothelial CAMs can be modulated by the tumor microenvironment. To this end, the various growth factors in the interstitial compartment of a growing tumor were obtained and the TIF collected from a human colon adenocarcinoma (LS174T) grown subcutaneously in mice with severe combined immunodeficiency disease (SCID mice). The resulting expression histograms, developed from targeted sampling fluorometry analysis of the stained monolayers (FIG. 1a), indicate that ICAM-1 and, to a lesser degree, VCAM-1 show increased expression in response to TIF exposure. E-selectin also showed a slight increase in expression; however, P-selectin expression was essentially unchanged. These expression experiments suggested a molecular mechanism for A-NK cell binding that could be tested by in vitro functional experiments.

Figure 2A:
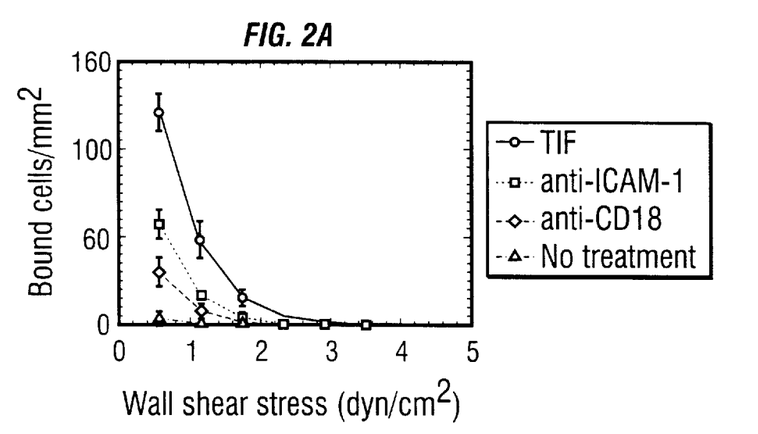
FIGS. 2a, 2b, 2c, 2d, 2e, and 2f are graphs showing the number of bound A-NK cells on HUVEC monolayers versus wall shear stress in the presence of TIF or various monoclonal antibodies.
Figure 2B:
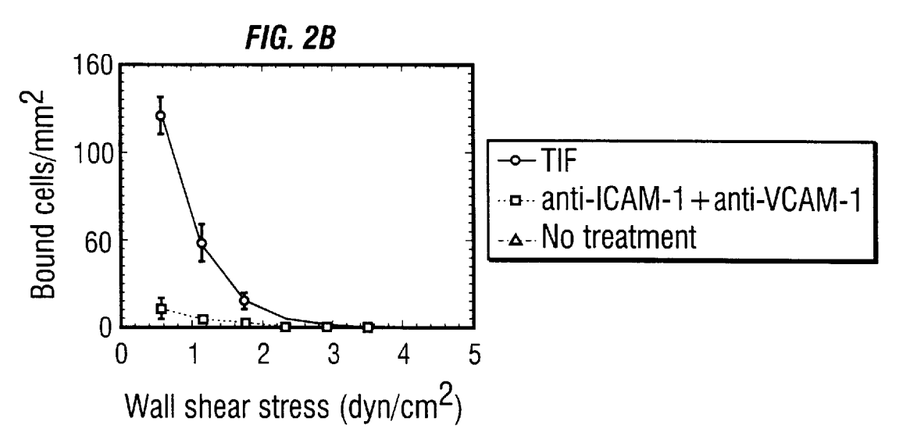
Figure 2C:
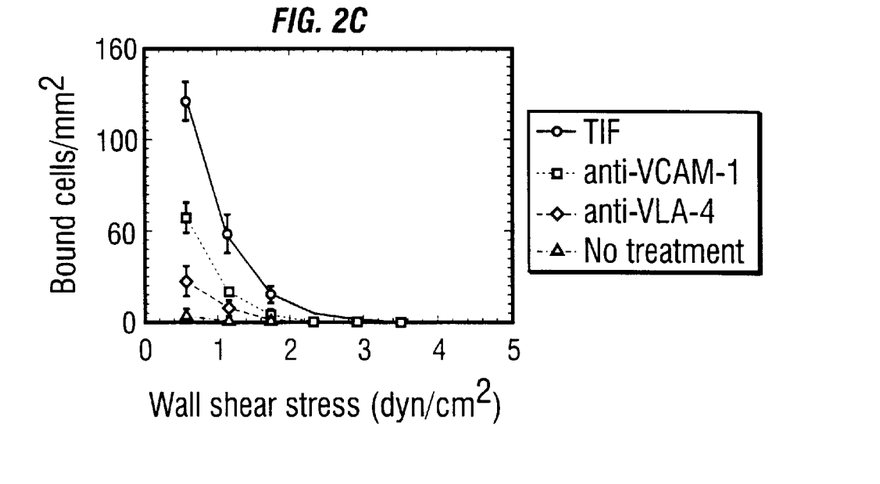
Figure 2D:
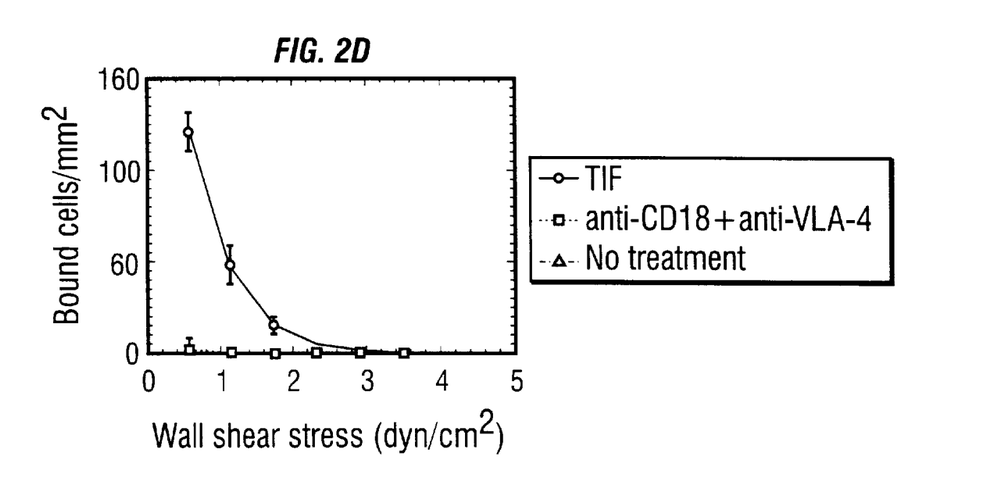
Figure 2E:
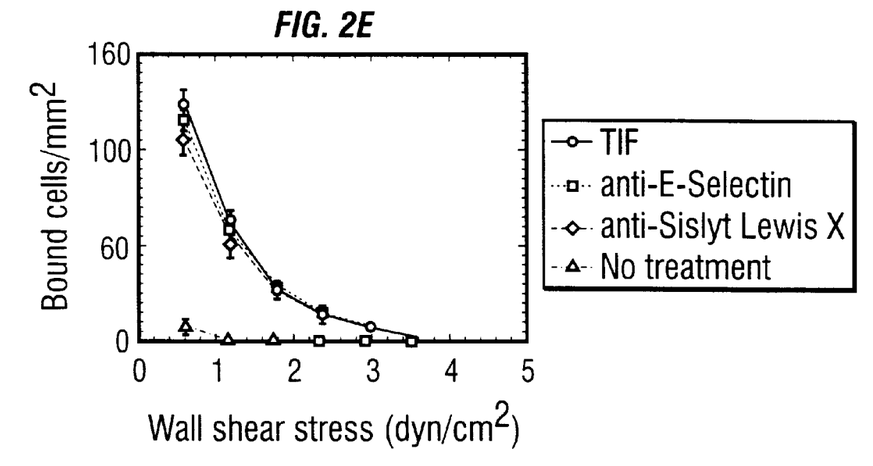
Figure 2F:
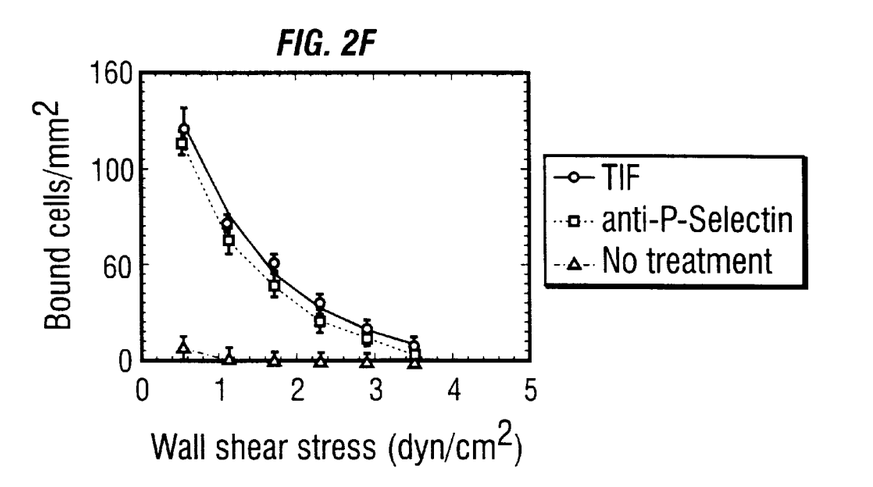

Tumor interstitial fluid modulation of A-NK adhesion. Parallel-plate flow chamber experiments were designed according to established procedures to determine whether the increased expression of CAMs would result in increased adhesion of A-NK cell populations under tumor blood flow conditions. Human umbilical vein endothelial cell (HUVEC) monolayers grown on slides were incubated with medium containing 1:50 dilution of TIF for 24 hours and were evaluated in the flow chamber for their ability to retain A-NK cells under shear stress conditions ranging from approximately 0.56 to 3.5 $dyn/cm^1$. These experiments (FIGS. 2a–2f) demonstrated that TIF exposure induced adhesion of A-NK cells to the endothelium. The greatest induction of adhesion occurred at shear stresses consistent with that in the microcirculation of tumors (between 2.0 and 0.5 $dyn/cm^2$). Antibody blocking experiments indicated that antibodies directed against either lymphocytes (CD18 or VLA-4) or endothelial CAMs (ICAM-1 or VCAM-1) were capable of significantly ($P<0.05$) reducing A-NK cell binding to treated monolayers (FIGS. 2a and 2c). However, blocking both CD18 and VLA-4 or ICAM-1 and VCAM-1 simultaneously was required to reduce binding to background levels (FIGS. 2b and 2d). Blocking ICAM-2 alone (not shown) also resulted in significant reductions ($P<0.05$) in bound cells. This result is consistent with the involvement of ICAM-2 in low-level binding to untreated monolayers at low shear stress, as it is constitutively expressed on non-activated endothelial cells. Blocking antibodies directed against E-selectin, P-selectin and sialyl Lewis X produced a slight but significant ($P<0.05$) reduction in A-NK cell adhesion (FIGS. 2e and 2f) only at the lowest level of shear stress examined.

To corroborate the in vitro findings that CD18/ICAM-1 and VLA-4/VCAM-1 mechanisms were principally responsible for the localization of A-NK cells in tumor vessels in vivo, tumors were grown in the cranial window preparations of immunocompetent (C3H) and SCID mice for adoptive cell transfer experiments. These studies used the LS174T tumor (which was also used for the collection of the TIF) in SCID mice and the MCaIV mammary adenocarcinoma (which was used in previous adoptive transfer studies) in C3H mice. We injected human A-NK cells treated with either (a) a combination of anti-CD18 and anti-VLA-4 monoclonal antibodies or (b) isotype control antibodies, into mice via the carotid artery, while monitoring the cranial window for the localization of the injected cells in vessels of the implanted tumors. Control IgG-treated cells showed significant retention in vessels of both the human LS174T tumor and the murine MCaIV tumor. Antibody blocking of the CD18 and VLA-4 on the A-NK cells before injection resulted in significant ($P<0.05$) reduction of the retained cells in both tumor types. Estimated shear rates, based on observed blood flow rates and vessel diameters, were not significantly different ($P<0.05$) for control and treatment groups. Mean shear rates ($\pm$ s.d.) for the LS174T tumors were $95\pm37/s$ and $85\pm42/s$ and for the MCaIV tumors were $110\pm41/s$ and $105\pm50/s$, in control and experimental groups, respectively.

As angiogenesis occurs in normal tissues (physiological) as well as in tumors (pathophysiological) we posed the hypothesis that A-NK cell binding is characteristic of angiogenic vessels in general and is not restricted to tumors. To test this possibility, cranial windows in SCID mice were implanted with fragments of syngeneic mesentery tissue and allowed to vascularize over a period of 4 weeks. These mice were then injected with A-NK cells via the carotid artery, and the vessel development was monitored for the localization of the injected cells. Three out of three preparations showed binding of the injected cells in the angiogenic vessels of the implant (FIG. 3e), indicating that injected A-NK cells recognized newly developing vessels in normal tissue.

Thus, we have discovered that basic fibroblast growth factor (bFGF) downregulates ICAM-1 and VCAM-1 on activated endothelium, thereby protecting this tissue from cytotoxic white cells (e.g., cytotoxic T-lymphocytes and Natural Killer cells). When new blood vessels are beneficially formed, e.g., following myocardial infarction, bFGF can be used to protect these new vessels from immune attack by cytotoxic lymphocytes.

Figure 3A:
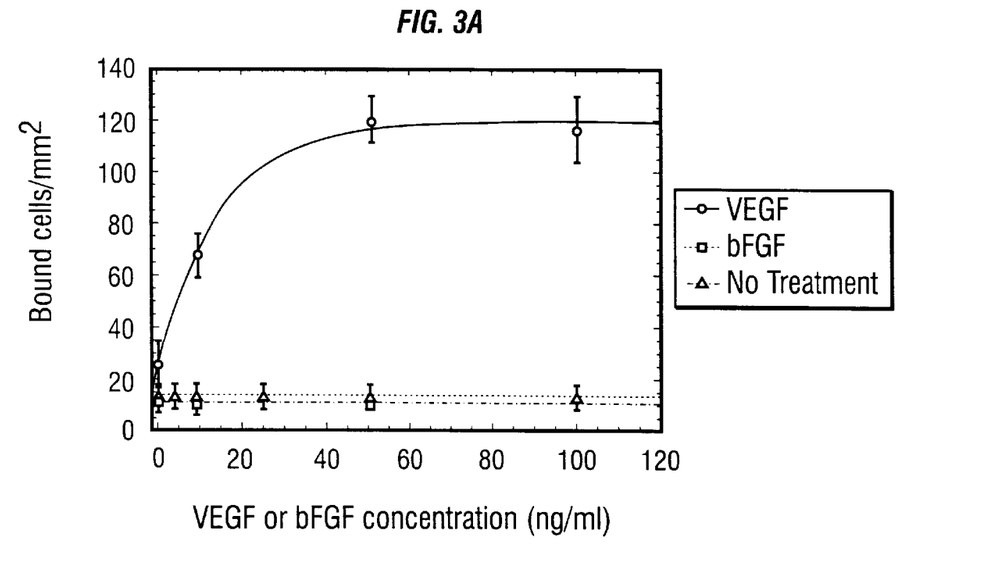
FIGS. 3a and 3b are graphs of the number of bound A-NK cells on HUVEC monolayers versus VEGF or bFGF concentration in the presence of varying amounts of VEGF, bFGF, or combinations thereof.
Figure 3B:
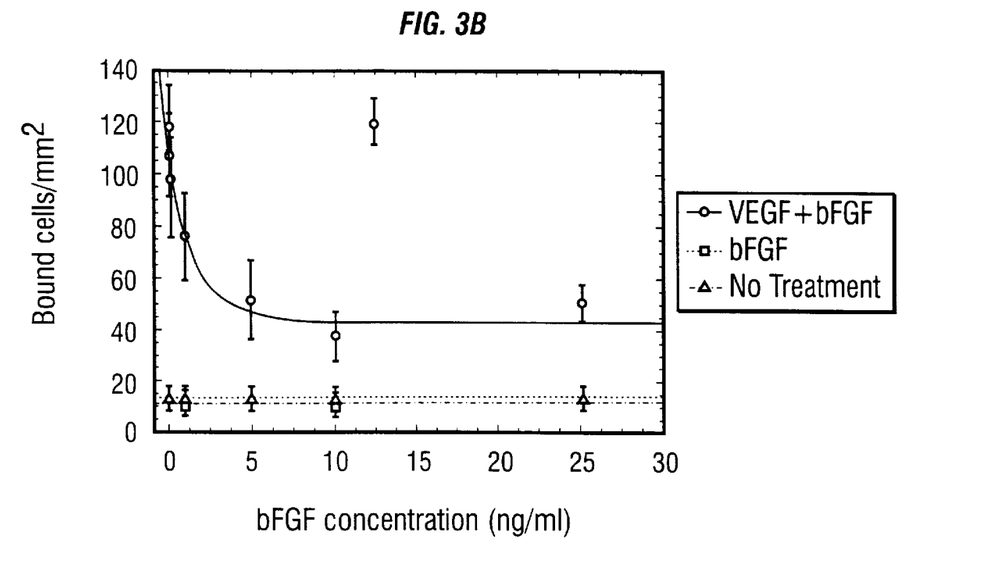

The increased ICAM-1, VCAM-1 and E-selectin expression of VEGF-treated HUVEC suggested that functional changes in A-NK cell adhesion to the endothelium may also be induced following VEGF treatment. This was tested with the in vitro flow chamber as described above. These experiments showed that VEGF treatment of HUVEC for 24 hours resulted in binding of A-NK cells at 1 $dyn/cm^2$ (FIG. 3a), in a dose-dependent manner up to 35 ng/ml. As was observed with TIF treatment, the greatest increase in A-NK cell binding was observed under shear stresses between 0.5 and 2 $dyn/cm^2$, and could be blocked with anti-ICAM-1 and anti-VCAM-1 antibodies. In contrast, bFGF treatment of HUVEC did not produce increased levels of A-NK cell binding at 1 $dyn/cm^2$ (FIGS. 3a and 3b). Both VEGF and bFGF may be present in the tumor microenvironment and are known to synergistically cause endothelial cell proliferation. Consequently, different concentrations of bFGF were added to medium supplemented with one concentration (35 ng/ml) of VEGF and placed on endothelial cells for 24 hours. Following the incubation, the endothelial monolayer showed changes in morphology (for example, cell elongation) that were consistent with activation into a proliferative state. Flow chamber experiments, however, indicated that bFGF significantly (P<0.05) reduced the adhesion of A-NK cells to treated endothelium at 1 dyn/cm$^2$ at all concentrations of bFGF greater than 0.5 ng/ml (FIG. 3b), with an optimal level of approximately 5 ng/ml.

The in vivo influence of bFGF on A-NK cell adhesion to tumor vasculature was tested in the cranial window model with the LS174T tumor. Cranial windows were implanted in SCID mice with the LS174T tumor as described above. At 8 to 12 days after the implantation, the cranial windows were opened and 10 μl bFGF (30 μg) in saline was placed into the windows of the experimental group (n=5). Saline (10 μl) alone was given to the control group. The number of adherent cells in each animal's tumor vessels was quantified, as were the shear rates. The number of bound A-NK cells in the tumors treated with saline was 14.5±1.9/mm$^2$ and with bFGF was 2.7±0.5/mm$^2$. Shear rates were 128.5±24.1/s and 109.5±22.9/s, respectively. The reduction in the number of bound cells was significant (P<0.05) and demonstrates that bFGF inhibits lymphocyte adhesion in vivo.

Regulation of adhesion by bFGF and VEGF. We have previously established that tumor vessels exhibit wide variability in their capacity to retain A-NK cell populations and to support leukocyte rolling. Because heterogeneous A-NK cell adhesion to tumor vessels could be observed when lymphocyte flux is held constant, blood flow heterogeneity in the tumor vasculature cannot account for adhesion variability. This suggests that the production of bFGF in wound repair or within tumors may provide varying degrees of protection to growing vessels by inhibiting adhesion of circulating lymphocytes to endothelial cells that have been exposed to VEGF or other adhesion-promoting angiogenesis factors, such as tumor necrosis factor-α (TNF-α). Like bFGF, transforming growth factor β (TGF-β) is an inducer of angiogenesis that has been reported to inhibit E-selectin expression and to decrease lymphocyte infiltration in response to an inflammatory stimulus. However, its effect is limited to E-selectin expression and not ICAM-1 or VCAM-1 expression. As demonstrated by antibody blocking of E-selectin in the flow chamber studies (FIG. 2e), E-selectin has a relatively small role in NK cell adhesion under dynamic conditions. Consequently, TGF-β alone may have only a minimal influence on NK cell adhesion in this setting. However, it is expected that TGF-β might act in concert with bFGF to inhibit CAM expression and lymphocyte adhesion during angiogenesis.

In immunocompetent hosts, angiogenesis factors, including bFGF, may be produced by infiltrating lymphocytes as well as tumor or hypoxic tissues in the tissue microenvironment. Hence, products of the immune response to a tumor or inflammatory site could potentially either accelerate or inhibit further lymphocyte infiltration. Our in vitro studies suggest that the concentration of bFGF required to produce a reduction in cellular adhesion molecule expression and suppression of lymphocyte binding is orders of magnitude less than the concentration that reproducibly elicits an angiogenic response in normal tissue. Thus, an amount of bFGF too small to produce a significant angiogenic response can still have a dramatic effect on cellular adhesion in the developing vasculature.

Differential adhesion with lymphocyte subsets. Paradoxically, in vitro flow chamber experiments performed with activated T cells (>90% CD3 cells), instead of A-NK cells and TIF-treated endothelial cells, failed to show the same degree of accumulation of the activated T cells on the treated monolayer (unpublished data) under identical experimental conditions. Although these experiments were not optimized to observe low numbers of binding T cells, it is possible that A-NK cells may have an augmented ability to localize in angiogenic vessels because of other structural or mechanical characteristics, in addition to their high level of integrin expression. In addition, it should be noted that although bFGF and VEGF could potentially alter the number of lymphocytes that enter the tumor through the tumor vasculature, they may have relatively little influence on cells entering from the surrounding normal tissue.

Unified mechanism for NK cell localization in tumor vessels. Natural killer cells are known for their antitumor or antiviral cytotoxic properties. We have previously proposed that NK cells may exert an antitumor influence through an antivascular mechanism (Sasaki et al., J. Natl. Cancer Inst. 53:433–437, 1991). The cytotoxic activity of NK cells on endothelium has been previously established and supports this potential mechanism. The work presented here (1) demonstrates the role of the tumor microenvironment in the induction of NK cell binding to endothelial cells; (2) establishes a role for VEGF in upregulating ICAM-1, VCAM-1 and E-selectin expression, facilitating the vascular recognition process by NK cells; and (3) shows that bFGF may provide a protective mechanism for angiogenic vessels in the presence of circulating cytotoxic lymphocytes.

Methods

Preparation of HUVEC cultures. Human umbilical vein epithelial cell cultures obtained from single cord harvests were maintained in growth medium (EGM, Clonetics, San Diego, Calif.) supplemented with 10% FCS. A standardized, commercially available medium was used to ensure reproducibility of our results. Cell monolayers for CAM expression assays were established in 8-well glass culture slides (Nunc-Labtech, Naperville, Ill.), which had been coated with 6 μg/cm$^2$ fibronectin (Sigma). Monolayers for use in functional binding assays were grown on 3"×1.5" glass slides (Fisher Scientific, Pittsburgh, Pa.) coated with fibronectin as described in Watson et al., Science 268:447–448 (1995). Monolayers were used within 48 h of seeding.

Collection of TIF. Tumor interstitial fluid was obtained from LS174T colon adenocarcinoma tumors (ATCC, Rockville, Md.) grown in 25 to 30-g nude mice by using an implanted semipermeable chamber. Interstitial fluid was collected from the chamber between 7 and 14 days following tumor implantation and immediately frozen at −70° C.

After HUVEC were grown to confluence in wells on fibronectin-coated glass slides, they were incubated for 24 hrs with a 1:50 dilution of the TIF, VEGF (35 ng/ml, Peprotech, Rocky Hill, N.J.), or bFGF (10 ng/ml, Gibco BRL, Grand Island, N.Y.) in RPMI 1640 (Fisher Scientific, Pittsburgh, Pa.) without serum and stained for expression of ICAM-1, ICAM-2, VCAM-1, E-selectin and P-selectin. Following treatment, the monolayers were fixed and stained as previously described. Antibodies used in these studies were as follows: anti-P-selectin (clone GA6; Becton Dickinson Inc., San Jose Calif.), anti-E-selectin (clone H18/7; Becton Dickinson Inc.), anti-VCAM-1 (clone 1G11; AMAC Inc., Westbrook, Me.), anti-ICAM-1 (CD54, clone 84H10; AMAC Inc.), anti-ICAM-2 (CD102, clone CBR-1C2/2; Endogen, Cambridge, Mass.), isotype control antibodies (IgG1, IgG2; Becton Dickinson Inc.); and goat-anti-mouse F(ab')$_2$ (Tago, Burlingame, Calif.). Antibody treatment of the HUVEC monolayers was done with 10 μg antibody in 0.5 ml culture medium. Images for quantification were obtained and processed according to published protocols and the results were displayed as fluorescent intensity histograms of the stained population with a minimum of 1500 cells sampled.

Preparation of activated natural killer cells. Human lymphocytes obtained from peripheral blood of normal donors were isolated, activated with 1000 U/ml of interleukin-2 (Cetus/Chiron, Emeryville, Calif.) and used to produce cultures of A-NK cells, according to a previously described method (Melder et al., Cancer Res 48:3461–3469 [1988]). The expanded NK cell cultures isolated from this procedure were typically 90–98% $CD56^+$, $CD3^-$ and <5% $CD3^+$ cells by flow cytometric analysis. The cells were labeled for fluorescence microscopy with 0.01 mM calcein in PBS for 15 min, washed and resuspended in Hank's balanced salt solution (HBSS) with $Ca^{++}$ and $Mg^{++}$.

Interaction of A-NK cells in suspension with HUVEC was studied in a parallel-plate flow chamber. This chamber permits the quantification of cell adhesion under controlled conditions of flow rate, shear stress and cell flux. The bulk cell concentration was fixed at 1×10 cells/ml in all in vitro experiments, and the cumulative bound cell density was determined in five fields at each level of shear stress. Antibody blocking of individual and multiple CAMs was used to evaluate their participation in the lymphocyte capture process. Antibodies used in these studies were as follows: anti-CD49d (clone HP2/1); anti-CD18 (clone 1B4, obtained from Karl Arfors); anti-sialyl-Lewis X (clone CSLEX1); antiE-selectin (clone H18/7; Becton Dickinson); anti-P-selectin (CD62P, clone GA6; Becton Dickinson); anti-VCAM-1 (clone 1G11; AMAC Inc.); anti-ICAM-1 (CD54, clone 84H10; AMAC Inc.); anti-ICAM-2 (CD102, clone CBR-1C2/2); and IgG1 and IgG2 isotype control antibodies (clones X40 and X39; Becton Dickinson Inc.). Lymphocytes were treated with 10 μg antibody/1.5×$10^7$ cells (antibody excess), and HUVEC monolayers were treated with 10 μg antibody in 0.1 ml culture medium. The adherent cell density in each experiment was determined as previously described. The mean and standard deviation for each binding density is shown from a single representative experiment of three to five runs. Significance was established with a t-test.

Dose-response experiments were also conducted with recombinant angiogenesis factors, either alone or in combination. A-NK cultures and HUVEC were prepared as before. Following treatment with VEGF, bFGF (Gibco BRL) or both (fixed VEGF concentration at 35 ng/ml and variable bFGF concentration), flow chamber experiments were performed at single flow rates corresponding to 1 dyn/$cm^2$ wall shear stress. Quantification of cell adhesion was performed as described above.

The cultured lymphocytes were labeled for fluorescence microscopy as described in Melder et al., Microvascular Res 50:35–44 (1995). Cranial window implantation and experimental observation were performed under anesthesia with ketamine (9 mg) and xylazine (0.9 mg) per 100 g body weight. Tumor cells from cultured LS174T, in vivo passaged MCaIV ( C3H mouse mammary carcinoma, Steele Laboratory, Dept. of Radiation Oncology, MGH), or normal syngeneic mesenteric tissue were implanted at the time of the window implantation. Tumors were used at 8–12 days and mesenteric tissue at 21–28 days following implantation. The interaction of injected cells with the vasculature of the tumor was observed and recorded through the transparent window in the cranium by fluorescence video-microscopy. Antibody blocking studies were done by incubating the cells with 10 μg of antibody for 30 min at 4° C. before injection using anti-CD49d (clone HP2/1) and anti-CD18 (clone IB4), as previously described. A cell that was stably arrested for at least 5 s was considered bound. The mean number of bound cells per millimeter was determined in 5 to 15 microscopic fields in each tumor and used to determine the mean number of bound cells for each experimental group. Significance was established with the t-test and Mann-Whitney test.

EXAMPLE 1 bFGF is a well-known human protein which is commercially available in recombinant form from a number of sources. It can be produced in commercially significant amounts by recombinant methods employing cultured cells. The cells can be prokaryotes (e.g., *E. coli*), or eukaryotes (e.g., yeast, insect cells, or mammalian cells). The nucleic acid molecules encoding bFGF and having appropriate expression control sequences can be introduced into the cultured cells by viral infection, receptor-mediated endocytosis, liposome fusion, or any other standard transfection technique. These cultured cells are particularly useful for producing recombinant bFGF encoded by the nucleic acid molecules they harbor. Extraction and purification of recombinant proteins produced by tissue culture cells can be performed with techniques well known in the art, including, for example, immunoaffinity purification.

A patient having a medical condition in which cytotoxic lymphocytes attack the endothelium as a result of VCAM-1 or ICAM-1 expression can be treated by administering to the patient a VCAM-1 or ICAM-1 downregulating amount of bFGF.

The method of the invention can be used to treat any medical conditions in which it is desirable to downregulate the two aforementioned vascular adhesion molecules. These conditions include sepsis, inflammation, cancer, and reperfusion injury. The invention can also be used to inhibit allograft or xenograft rejection (e.g., rejection of kidney or heart transplants), as well as to inhibit graft-versus-host disease which can occur when cytotoxic lymphocytes in the graft attack the host in which the graft is implanted.

Administration of bFGF according to the invention can be carried out according to any of a number of standard methods, including intravenous, subcutaneous, intra arterial, intraperitoneal, transmucosal, oral, and intrapulmonary administration. In addition, an implant which allows slow release can be used to administer the bFGF to the patient. The bFGF can be combined with one or more additional active agents, such as TGF-β.

bFGF according to the invention is administered in dosages comparable to dosages of other recombinant proteins used therapeutically for similar purposes. Typical dosage levels would be designed to produce a serum concentration of about 1–100 ng/ml. Optimal dosage for a given patient depends upon weight, age, gender, etc., and can be determined by one of ordinary skill in the art.

The data obtained from cell culture assays and animal studies can be used in formulating a range of bFGF dosage for use in humans. The dosage lies preferably within a range of circulating concentrations that include the $ED_{50}$ with little or no toxicity. The dosage may vary within this range depending upon the dosage form employed and the route of administration utilized. The therapeutically effective dose can be estimated initially from cell culture assays. A dose may be formulated in animal models to achieve a circulating plasma concentration range that includes the $IC_{50}$ (that is, the concentration of bFGF which achieves a half-maximal inhibition of symptoms) as determined in cell culture. Such information can be used to more accurately determine useful doses in humans. Levels in plasma may be measured, for example, by high performance liquid chromatography.

Pharmaceutical compositions containing bFGF for use in accordance with the methods of the present invention may be formulated in conventional manner using one or more physiologically acceptable carriers or excipients.

Thus, bFGF may be formulated for administration by inhalation or insufflation (either through the mouth or the nose) or oral, buccal, pulmonary, nasal, parenteral, or rectal administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

For administration by inhalation, the bFGF used according to the methods of the present invention is conveniently delivered in the form of an aerosol spray presentation from pressurized packs or a nebulizer, with the use of a suitable propellant. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The bFGF can be formulated for parenteral administration by injection, for example, by bolus injection or continuous infusion. Formulations for injection may be presented in unit dosage form, for example, in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

The bFGF can also be formulated in rectal compositions such as suppositories or retention enemas, for example, containing conventional suppository bases such as cocoa butter or other glycerides.

In addition to the formulations described previously, bFGF may also be formulated as a depot preparation. Such long acting formulations may be administered by implantation (for example subcutaneously or intramuscularly) or by intramuscular injection. Thus, for example, bFGF can be formulated with suitable polymeric or hydrophobic materials (for example as an emulsion in an acceptable oil) or ion exchange resins, or as sparingly soluble derivatives, for example, as a sparingly soluble salt.

The bFGF can, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The therapeutic compositions used in the methods of the invention can also contain a carrier or excipient, many of which are known to skilled artisans. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol.

Targeting of bFGF to vascular edothelium may be achieved by local injection of liposomes that contain bFGF. For enhanced targeting, the liposomes may be coated with molecules which function as ligands of endothelium-specific receptors.

EXAMPLE 2 bFGF can be used as a perfusion agent for pretreatment of allografts or xenografts. For example, before a new kidney is transplanted into a host, the donor kidney (and in particular, the blood vessels thereof) can be bathed in a physiological buffer containing sufficient bFGF which is effective in reducing host leukocyte adhesion to the endothelium of the new kidney. This reduction in leukocyte adhesion may ameliorate host rejection of the kidney.

EXAMPLE 3

Another way to introduce bFGF into a patient, or into an organ, tissue or cell preparation to be transplanted, is by overexpressing within the cells of the patient or transplant a nucleic acid construct which includes expression control sequences operably linked to a sequence encoding the protein. The nucleic acid construct is derived from a non-replicating linear or circular DNA or RNA vector, or from an autonomously replicating plasmid or viral vector; or the construct is integrated into the host genome. Any vector that can transfect a mammalian cell may be used in the methods of the invention. Methods for constructing expression vectors are well known in the art (see, e.g., *Molecular Cloning: A Laboratory Manual*, Sambrook et al., eds., Cold Spring Harbor Laboratory, 2nd Edition, Cold Spring Harbor, N.Y., 1989).

In these vectors, promoters are operably linked to the nucleic acid sequence encoding bFGF. Any promoter that can direct a high level of transcription initiation in the target cells (e.g., vascular endothelial cells) may be used in the invention. Non-tissue specific promoters, such as the cytomegalovirus (DeBernardi et al., Proc. Natl. Acad. Sci. USA 88:9257–9261, 1991, and references therein), mouse metallothionine I gene (Hammer et al., J. Mol. Appl. Gen. 1:273–288, 1982), HSV thymidine kinase (McKnight, Cell 31:355–365, 1982), and SV40 early (Benoist et al., Nature 290:304–310, 1981) promoters may be used in methods of the invention, as overexpression of bFGF in the methods of the invention would not be expected to adversely affect transfected cells. The above-described nucleic acid constructs and vectors can be introduced into target cells by any standard method: e.g., as naked DNA, or by liposome fusion, biolistic transfer, electroporation, erythrocyte ghosts, or microsphere methods (microparticles; see, e.g., U.S. Pat. No. 4,789,734; U.S. Pat. No. 4,925,673; U.S. Pat. No. 3,625,214; Gregoriadis, *Drug Carriers in Biology and Medicine,* pp. 287–341, Academic Press, 1979). Alternatively, one can employ a viral-based vector as a means for introducing the nucleic acid into the cells of the animal. Preferred viral vectors include those derived from replication-defective hepatitis viruses (e.g., HBV and HCV), retroviruses (see, e.g., WO89/07136; Rosenberg et al., N. Eng. J. Med. 323(9):570–578, 1990), adenovirus (see, e.g., Morsey et al., J. Cell. Biochem., Supp. 17E, 1993), adeno-associated virus (Kotin et al., Proc. Natl. Acad. Sci. USA 87:2211–2215, 1990), replication defective herpes simplex viruses (HSV; Lu et al., Abstract, page 66, Abstracts of the Meeting on Gene Therapy, Sep. 22–26, 1992, Cold Spring Harbor Laboratory, Cold Spring Harbor, N.Y.), canary pox virus, and any modified versions of these vectors.

EXAMPLE 4

Rather than introduce the vector itself directly into the patient or organ, delivery of bFGF can be accomplished by transfecting cells (e.g., primary cells of the patient) in vitro with an expression vector encoding bFGF; culturing the cells to produce a stably transformed, uniform population; and implanting the bFGF-secreting population of cells into the patient.

Other embodiments are within the following claims.

What is claimed is:

1. A method of treating a condition involving vascular adhesion of cytotoxic white cells, comprising:
   identifying an animal suspected of having a condition involving vascular adhesion of cytotoxic white cells; and
   administering to the animal an amount of bFGF sufficient to decrease cell surface expression of at least one of ICAM-I, VCAM-I and E-selectin on endothelial cells, thereby reducing adhesion of cytotoxic white cells to vascular endothelium.

2. The method of claim 1 wherein the condition is sepsis.

3. The method of claim 1 wherein the condition is inflammation.

4. The method of claim 1 wherein the condition is ischemia-reperfusion injury.

5. The method of claim 1 wherein the condition is transplant rejection.

6. The method of claim 5 wherein the transplant comprises an organ.

7. The method of claim 5 wherein the transplant comprises a tissue.

8. The method of claim 5 wherein the transplant comprises a cell.

9. The method of claim 1 wherein the bFGF is administered by introducing into the animal an expression vector.

10. The method of claim 9, wherein the expression vector is within a cell, and the cell is introduced into the animal.

11. The method of claim 1 wherein the bFGF is administered systemically.

12. The method of claim 1 wherein the bFGF is administered intravenously.

13. The method of claim 1 wherein the bFGF is administered via an implant.

14. The method of claim 13 wherein the implant provides slow release of the bFGF.

15. The method of claim 1 wherein the animal is a human.

16. A method of reducing adhesion of cytotoxic white cells to vascular endothelium of a transplant, comprising:
   treating the transplant ex vivo with an amount of bFGF sufficient to decrease cell surface expression of at least one of ICAM-I, VCAM-I, and E-selectin on endothelial cells of the transplant, thereby reducing adhesion of cytotoxic white cells to vascular endothelium of the transplant.

17. The method of claim 16 wherein the transplant comprises an organ.

18. The method of claim 16 wherein the transplant comprises a tissue.

19. The method of claim 16 wherein the transplant comprises a cell.

20. The method of claim 16 wherein the bFGF is administered by perfusion of the transplant.

21. The method of claim 16 wherein the bFGF is administered by introducing into the transplant an expression vector encoding bFGF.

22. The method of claim 16 wherein the bFGF is administered via an implant.

* * * * *

UNITED STATES PATENT AND TRADEMARK OFFICE
CERTIFICATE OF CORRECTION

PATENT NO. : 6,010,712
DATED : JANUARY 4, 2000
INVENTOR(S) : RAKESH K. JAIN ET AL.

It is certified that error appears in the above-identified patent and that said Letters Patent is hereby corrected as shown below:

On the title page in the drawing, on the third histogram, change "B-selectin" to --E-selectin-- as described in the Brief Description of the Drawings;

On sheet 1 (Fig. 1A) of the figures, change "B-selectin" to --E-selectin-- as described in the Brief Description of the Drawings;

On Sheet 2 (Fig. 1B) of the figures, change "B-selectin" to --E-selectin-- as described in the Brief Description of the Drawings;

On Sheet 6 (Fig. 2E) of the figures, in the box on the right, change "anti-Sislyt" to --anti-Sialyl--; and On Sheet 7 (Fig. 3B) of the figures, delete the VEGF + bFGF symbol directly under the top line in the center of the graph.

Signed and Sealed this

Twenty-seventh Day of March, 2001

*Attest:*

NICHOLAS P. GODICI

*Attesting Officer*   *Acting Director of the United States Patent and Trademark Office*